US00PP09815P

United States Patent [19]

Bourke et al.

[11] Patent Number: Plant 9,815

[45] Date of Patent: Mar. 4, 1997

[54] CAMPANULA PLANT NAMED CHETTLE CHARM

[75] Inventors: Janet E. Bourke; John P. C. Bourke, both of Dorset, England

[73] Assignee: Blooms of Bressingham Ltd., Norfolk, England

[21] Appl. No.: 544,696

[22] Filed: Oct. 18, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A new and distinct cultivar of Campanula plant named Chettle Charm, characterized by its distinct white, blue-tinged flowers, with flowering beginning in June and continuing into August; clump forming low growing habit making it ideal for use in borders or containers, vigorous growth habit, and its tall flowered spikes which make excellent cut flowers.

2 Drawing Sheets

The present invention relates to a new and distinct cultivar of hardy perennial herbaceous plant of the genus Campanula, a member of the Campanulaceae family, and known by its cultivar name Chettle Charm.

Chettle Charm was discovered as a seedling from a breeding program carried out by inventors John P. C. Bourke and Janet E. Bourke at Chettle House, Chettle, Blandford in the County of Dorset, England. The female parent was a presently unidentified cultivar of the species *Campanula persicifolia* and the male parent was the cultivar alba of the same species. The aim of the program was to produce a new cultivar which would not only be attractive in a garden situation but would also be ideal as a cut flower, combining the colors of the parents with the reliability of the male parent Alba.

The new cultivar was asexually reproduced by division by the inventors in Chettle, Blandford, England, and has been found to retain its characteristic from generation to generation.

Chettle Charm is particularly characterized by its large flowered spikes which make excellent cut flowers. The flowers, of classic *C. persicifolia* type, are edged with blue gradually fading to white at the center. Like Alba, the new cultivar forms evergreen mounds of narrow basal rosettes, a pleasing backdrop to the tall slender spikes which emerge with tight green buds which gradually open to reveal the porcelain blue and white flowers. The plant thrives best in full sun but will tolerate part shade in well drained soil that does not become too dry.

BRIEF DESCRIPTION OF THE PHOTOGRAPHS

DETAILED PLANT DESCRIPTION

Figure 1:
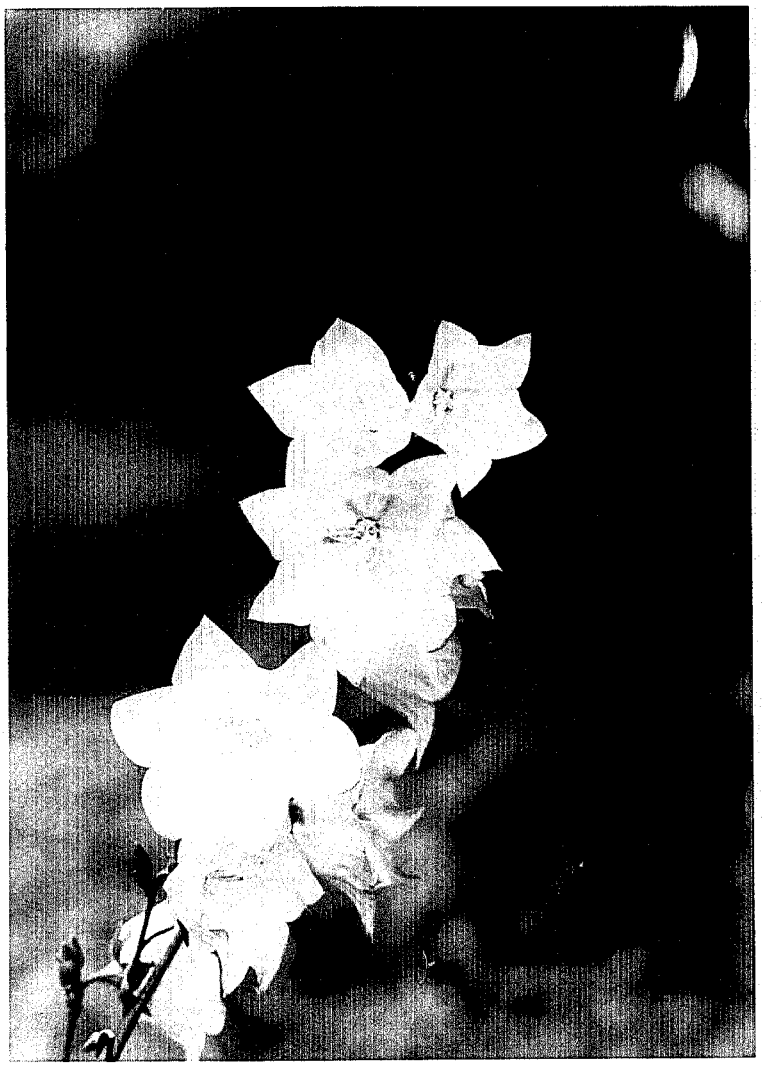
FIG. 1 is a close up view of the plant emphasizing the clusters of white flower cups with blue edging.
Figure 2:
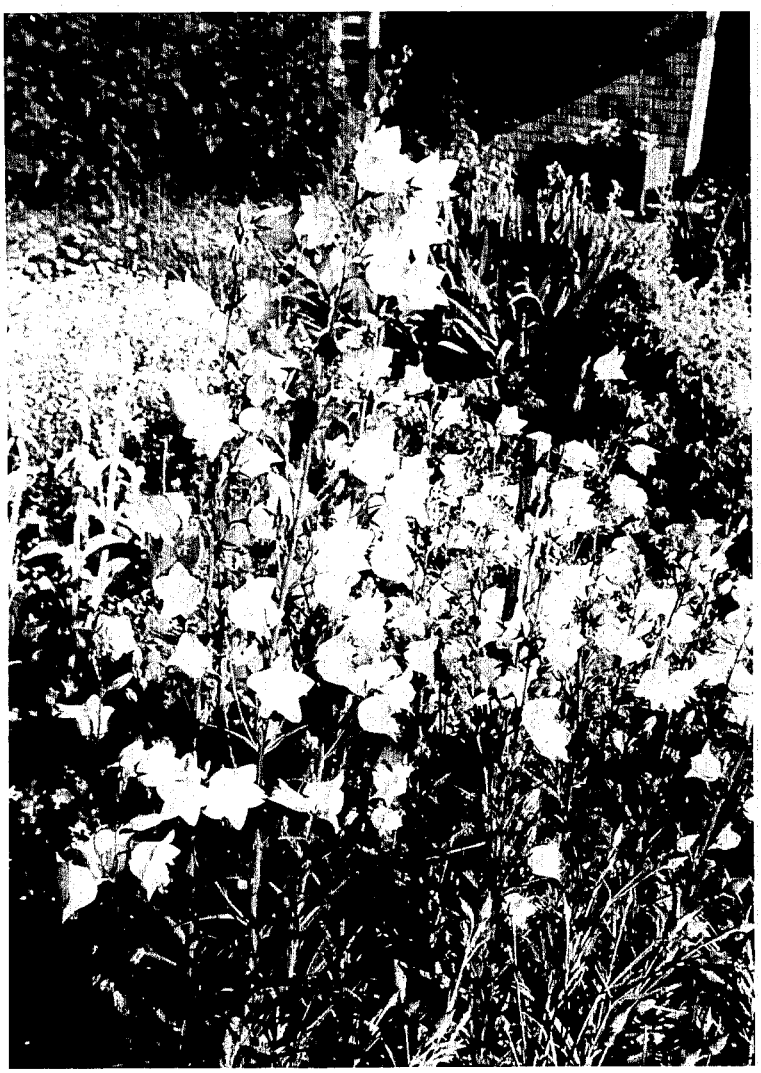
FIG. 2 is a view of the plant growing in a border setting.

The following is a detailed description of the new cultivar, with color determinations and comparisons being based on The Royal Horticultural Society Colour Chart.

Origin: Seedling selection.

Parentage: A cross between a unidentified cultivar of *Campanula persicifolia* as the female parent and the *Campanula persificolia cultivar Alba as the male parent.*

Habit: Clump forming.

Size: Mature plants are 90–120 cm (36–48 inches) in height with a spread of 40 cm (16 inches).

Plant vigor: A perennial that shows vigorous and health growth throughout Great Britain.

Root system: Fibrous.

Blooming habit: Large showy white, blue-tinged flowers borne on erect racemose stems arising from base of the plant.

Blooming period: From June continuing into August.

Hardiness: Winter hardy throughout the British Isles. The plant has not been fully tested for maximum summer temperature tolerance above 32° C. (90° F.).

FOLIAGE

Arrangement: Glabrous with linear lanceolate to subulate. Finely and remotely crenulate stem leaves.

Type: Evergreen perennial.

Texture: Smooth and without hairs.

Length: 10–15 cm.

Width: 2 cm.

Petiole length: 2 cm.

Margins: Crenate.

Apex: Acuminate.

Base: Truncate.

FLOWERS

Petal:

*Count.*—Six of equal size.

*Shape.*—Cup shaped.

Flower:

*Type.*—Racemose.

*Size.*—6 cm.

Borne: On erect stems rising from the base.

Carpels: 3–5 celled.

Stamens: Yellow 1B in color.

COLOR CHARACTERISTICS

Foliage:

*Mature leaves.*—Upper surface 131A; under surface 137C.

Flowers:

*Mature flowers.*—Outside and inside edges on petals are 97A, fading towards the center which is 155B.

It is claimed:

1. A new and distinct cultivar Campanula plant named Chettle Charm, as shown and described.

* * * * *